United States Patent [19] [11] Patent Number: 4,972,848
Di Domenico et al. [45] Date of Patent: Nov. 27, 1990

[54] MEDICAL ELECTRICAL LEAD WITH POLYMERIC MONOLITHIC CONTROLLED RELEASE DEVICE AND METHOD OF MANUFACTURE

[75] Inventors: Edward D. Di Domenico, Anoka; Christopher M. Hobot, Tonka Bay; Kenneth B. Stokes, Minneapolis; Arthur J. Coury, St. Paul; Phong D. Doan, Shoreview; Richard D. Sandstrom, Scandia, all of Minn.

[73] Assignee: Medtronic, Inc., Minneapolis, Minn.

[21] Appl. No.: 398,220

[22] Filed: Aug. 23, 1989

[51] Int. Cl.⁵ .............................................. A61N 1/00
[52] U.S. Cl. .................................. 128/785; 128/419 P
[58] Field of Search .................... 128/785, 419 P, 783, 128/784, 786, 642

[56] References Cited

U.S. PATENT DOCUMENTS

| | | | |
|---|---|---|---|
| H356 | 11/1987 | Stokes et al. | 128/785 |
| 4,106,512 | 8/1978 | Bisping | 128/418 |
| 4,217,913 | 8/1980 | Dutcher | 128/785 |
| 4,506,680 | 3/1985 | Stokes | 128/786 |
| 4,577,642 | 3/1986 | Stokes | 128/784 |
| 4,606,118 | 8/1986 | Cannon et al. | 29/825 |
| 4,711,251 | 12/1987 | Stokes | 128/784 |
| 4,819,661 | 4/1989 | Heil, Jr. et al. | 128/786 |
| 4,886,074 | 12/1989 | Bisping | 128/785 |

Primary Examiner—Lee S. Cohen
Assistant Examiner—Scott Getzow
Attorney, Agent, or Firm—Reed A. Duthler

[57] ABSTRACT

A cardiac pacing lead or other stimulation lead carrying a steroid compounded within a polymer matrix. The steroid is dispersed in thermoplastic or thermoset polyurethane or polyurea forming monomers or prepolymers. The mixture is then chain extended by addition of the appropriate difunctional or multifunctional isocyanate, hydroxyl or amine curing agent to form a solid polymer. The resulting formulation is molded or cast into a desired shape, and incorporated in the distal end of a medical electrical lead, adjacent to or within the electrode. In a preferred embodiment, the medical lead employs an extendable helix which is screwed into body tissue, and the polymer containing the drug takes the form of a generally dimensionally stable annular member mounted to the lead, encircling the helix.

9 Claims, 1 Drawing Sheet

MEDICAL ELECTRICAL LEAD WITH POLYMERIC MONOLITHIC CONTROLLED RELEASE DEVICE AND METHOD OF MANUFACTURE

BACKGROUND OF THE INVENTION

The present invention relates generally to electrical medical leads, and more particularly to stimulation leads of the type which dispense a steroid or other drug adjacent to the stimulation site. The invention is particularly useful in the context of a cardiac pacing lead.

Delivery of a drug at the stimulation site of an implantable pacing lead is disclosed in U.S. Pat. No. 4,711,251, issued to Stokes. A particularly desirable configuration for such a lead is disclosed in U.S. Pat. No. 4,506,680, also issued to Stokes. In this configuration, the drug to be dispensed, a glucocorticosteroid, is compounded with silicone rubber based medical adhesive, and located within a chamber within the distal end of the stimulation electrode. The steroid acts as an anti-inflammatory agent, reducing the effects of inflammation due to the reaction of the tissue to the stimulation electrode.

Alternative embodiments of stimulation electrodes which elute a steroid or other drugs are disclosed in U.S. Pat. No. 4,606,118 issued to Cannon et al and in U.S. Pat. No. 4,577,642 issued to Stokes. A myocardial pacing lead adapted to deliver steroid at the stimulation site is disclosed in Statutory Invention Registration No. H356, by Stokes et al in which a steroid is delivered through a barbed electrode to a delivery point within the myocardium.

SUMMARY OF THE INVENTION

The lead disclosed in U.S. Pat. No. 4,506,680, issued to Stokes, employs a monolithic controlled release device (MCRD) in which sodium dexamethasone phosphate is compounded in silicone rubber based medical adhesive. While this provides a workable controlled release device, it swells significantly during use. As a result, in the electrode disclosed in that patent, the MCRD is contained within a hollow chamber within the electrode, and provided with an internal expansion space into which the release device may expand.

The present invention employs a dimensionally stable monolithic controlled release device (MCRD) fabricated of a polymer such as a polyurethane, polyurea or polyurethane polyurea. The MCRD does not expand significantly when exposed to body fluid and therefore may be mounted exposed to or on the exterior surface of a pacing lead. The release device may be cast or molded to a desired shape, and may be located adjacent to or on the electrode surface. The MCRD may be fabricated as a polymer composite which is readily adhesively bonded to other components of the lead. For example, a polyurethane MCRD is readily adhered to a pacing lead having a polyurethane insulative sheath, or molded polyurethane components adjacent to the electrode. The MCRD may also be mechanically attached to the pacing lead.

In preferred embodiments, the release device is configured as an annular member encircling the fixation helix in an endocardial screw-in lead. This allows the steroid to elute in the vicinity of the electrode, without requiring delivery of the steroid through the electrode. The MCRD may be located within a lumen or recess at the distal tip of the lead. Steroid may then elute from the bulk of the MCRD into body fluid within the lumen, and then contact the tissue adjacent to the tip of the lead. By limiting the surface available for elution primarily to the interior of the lead, dissipation of the steroid into the bloodstream is reduced. Because the MCRD is generally dimensionally stable, it will not expand to the degree that it interferes with the operation of the fixation helix.

DETAILED DESCRIPTION OF THE INVENTION

Figure 1:
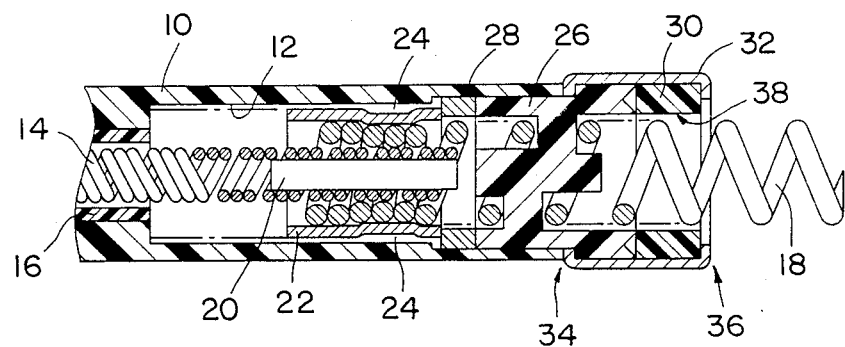
FIG. 1 is a side, cutaway view of a first embodiment of a pacing lead employing a monolithic controlled release device according to the present invention.

FIG. 1 is a side, cutaway view of the distal end of a cardiac pacing lead employing a monolithic controlled release device according to the present invention. The remainder of the structure of the lead may correspond to that illustrated in the article "The Impact of Pending Technologies on a Universal Connector Standard", by Doring and Flink, published in *PACE*, November-December 1986, part 2, pp. 1186-1190, incorporated herein by reference in its entirety. Additional appropriate configurations for the proximal end of the pacing lead are disclosed in U.S. patent application Ser. No. 07/304,756, for a "MEDICAL ELECTRICAL LEAD CONNECTOR", by Ufford et al, filed Jan. 31, 1989, also incorporated herein by reference in its entirety. Alternatively, any other conventional pacing lead construction may be used, provided that it includes a freely rotatable coiled conductor extending through the lead body.

The distal end of the pacing lead illustrated in FIG. 1 carries the electrode assembly. The electrode assembly includes an electrode head comprising head member 10, electrode guide 26 and sleeve 32. Head member 10 is molded plastic and includes an internal cylindrical lumen 12. Entering the lumen 12 from the proximal end is an elongated coiled conductor 14. As illustrated, conductor 14 takes the form of a multifilar coil having three individual filars. However, other coil configurations might also be used. Surrounding coil 14 is a tubular insulative sheath 16, which extends to the proximal end of the lead. Coil 14 is mounted so that it rotates freely within sheath 16. Exiting the distal end of the lead is a sharpened helix 18, which is screwed into the tissue to be stimulated and functions as an electrode. Helix 18 and coil 14 are mechanically and electrically maintained in contact with one another by means of crimps 24, which mechanically compress the proximal end of helix 18 and the distal end of coil 14 between crimping core 20 and crimping sleeve 22. As coiled conductor 14 is rotated in a counterclockwise direction as viewed from the distal end of the lead, helix 18 is screwed out of the distal end of the lead rotating around electrode guide 26. A radiopaque indicator ring 28 is located within lumen 12 of lead member 10, and serves to indicate the position of helix 18. By using a fluoroscope, the physician can determine the distance between crimping sleeve 22 and indicator ring 28, and thereby determine the distance helix 18 has been screwed out of the lead.

A monolithic controlled release device 30 is located at the distal end of electrode guide 26. MCRD 30 takes the form of an annulus surrounding helix 18. MCRD 30 is mounted against the distal end of electrode guide 26 and is surrounded by a platinum sleeve 32, which is provided with a circumferential, die formed shoulder 34 at its proximal end, retaining sleeve 32 to electrode guide 26. A die formed shoulder at the distal end of sleeve 32 assists in retaining MCRD 30.

In the disclosed embodiment, sleeve 32 is electrically isolated from any of the conductors of the lead. However, in alternative embodiments, sleeve 32 might be electrically coupled to conductor 14 or an additional conductor and used as an electrode. In some alternative embodiments in which sleeve 32 is used as an electrode, helix 18 may be electrically inactive and used only to affix the distal end of the lead to heart tissue. Screw-in leads employing electrodes mounted to the end of the lead body and electrically isolated fixation helices are disclosed in U.S. Pat. No. 4,217,913, issued to Dutcher, and in U.S. Pat. No. 4,209,019, issued to Dutcher et al, both of which are incorporated herein by reference in their entirety.

Helix 18 is screwed into the body tissue, with sleeve 32 lying adjacent the tissue. In use, the cavity 38, defined by the interior of electrode guide 26 and MCRD 30, becomes filled with body fluid, and the drug incorporated in MCRD 30, preferably an antiinflammatory or antiarrhythmic drug, elutes into the body fluid and thereafter into the body tissue adjacent the end of sleeve 32. Helix 18 tends to hold the body tissue against the distal end of sleeve 32. This allows sleeve 32 to largely retain the steroid eluted from MCRD 30 in the immediate vicinity of the tissue, rather than allowing it to be dispersed in, or washed away by the bloodstream or other body fluid.

Figure 2:
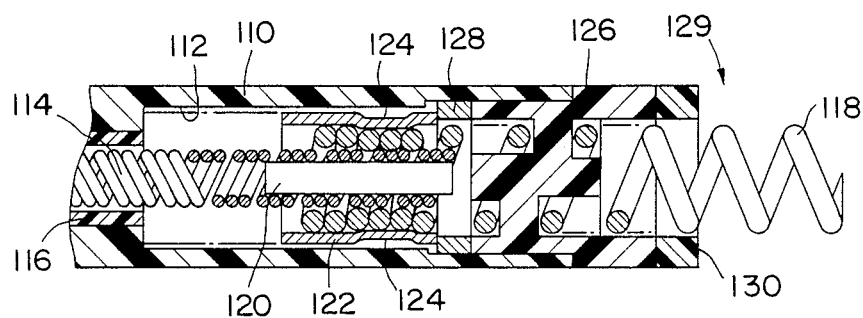
FIG. 2 is a side, cutaway view of an alternate embodiment of a lead employing the monolithic controlled release device of the present invention.

FIG. 2 shows a side cutaway view of the distal end of an alternate embodiment of a pacing lead according to the present invention. The distal end of the pacing lead carries the electrode assembly. The electrode assembly includes an electrode lead comprising a molded plastic head member 110 and a molded plastic electrode guide 126. Entering the lumen 112 of head member 110 from the proximal end is an elongated coiled conductor 114. Surrounding coil 114 is an insulative sheath 116, which extends to the proximal end of the lead. Coil 114 is mounted so that it rotates freely within sheath 116. Exiting the distal end of the lead is a fixation helix 118. Helix 118 and coil 114 are coupled to one another by means of a crimping sleeve 122 and a crimping core 120, which function similarly to the corresponding parts illustrated in FIG. 1. Helix 118 is screwed out the distal end of the lead by rotation of coil conductor 114. An indicator ring 128 serves to indicate the extent to which helix 118 has been screwed out of the distal end of the lead.

In this embodiment, the configuration of electrode guide 126 differs from that of electrode guide 26 (FIG. 1), in that MCRD 130 is maintained affixed to electrode guide 126 by means of adhesive. In this configuration, it is especially advantageous that electrode guide 126 and MCRD 130 are made of similar plastics in order to facilitate adhesive bonding of MCRD 130 to electrode guide 126. In the context of a cardiac pacing lead, MCRD 130 and guide 126 may both be fashioned of polyurethanes. In all other respects, the lead functions identically to the lead illustrated in FIG. 1.

Monolithic controlled release devices appropriate for use in conjuction with the present invention are fabricated by first mixing the steroid or other drug to be delivered with the monomer or prepolymer components of the MCRD. The mixture is then subjected to polymerizing conditions, causing the formation of a polymeric MCRD which includes the drug to be delivered.

In general, the composite MCRD should be relatively dimensionally stable so that it does not exhibit undue swelling when exposed to body fluid. Appropriate polymers for achieving this result would include polyurethanes, polyureas, polyurethane-polyureas, epoxies or the like. Examples of appropriate methods of fabrication of monolithic controlled release devices according to the present invention are set forth below. The polymer may be crosslinked or non-crosslinked and the degree of crosslinking may be useful in varying the elution rate. Other variables which may affect the elution rate include steroid loading, steroid particle size, and the configuration of the soft segment of the polymer.

In the examples which follow, the drug incorporated into the monolithic controlled release device is sodium dexamethasone phosphate, an antiinflammatory glucocorticosteroid. In all of the examples set forth below, it is important to dry the steroid prior to incorporation into the polymer to avoid undesired side reactions. An adequate procedure for drying the steroid is to place the steroid powder under vacuum and dry it for four days at 50° C. The vacuum may then be broken to dry nitrogen. The steroid should then be placed in a desiccator under vacuum for a minimum of four additional days at room temperature. The steroid should remain in the desiccator until immediately prior to use. The vacuum in the desiccator should be broken to dry nitrogen immediately before incorporation of the steroid into the MCRD formulation. In methods according to the following examples, it is preferable that the reactions take place under nitrogen in order to avoid unwanted side reactions. Storage of prepolymers and curing of polymers should likewise be done under nitrogen purge or vacuum.

EXAMPLE 1

A polyurethane containing sodium dexamethasone phosphate was produced according to a two step polymerization method, such as that disclosed in U.S. patent application Ser. No. 251,418, by Coury et al, filed Sept. 30, 1988, and incorporated herein by reference in its entirey.

Step 1

11.18 grams (0.075 Eq.) of 9-hydroxymethyl octadecanol, supplied by Henkel Corp. and 10.58 grams (0.178 Eq.) of 1,6-hexane diol were dried under vacuum at 100° C., and combined with 49.82 grams of dimer diisocyanate (0.167 Eq.) which had previously been heated to 100° C. The mixture was stirred until clear, and then allowed to cure under nitrogen 12 to 16 hours at 50° C. The resulting prepolymer was stored under nitrogen at ambient temperature.

Step 2

10.51 grams (0.012 Eq.) of the hydroxyl terminated prepolymer formed above were mixed with 7.02 grams (0.047 Eq.) of 9-hydroxymethyl octadecanol which had previously been heated to 150°-200° F., and the mixture was stirred. 9.53 grams of sodium dexamethasone phosphate, previously dried as discussed above, were slowly mixed into the above mixture. After incorporation of the steroid, 4.94 grams (0.059 Eq.) of 1,4-cyclohexane diisocyanate were stirred into the mixture, and the resulting mixture was placed in a 200° F. oven until the cyclohexane diisocyanate had dissolved completely. The mixture was then placed into a picture frame mold and allowed to cure overnight at 50° C. under nitrogen purge to produce a film approximately 0.038 inches thick.

EXAMPLE 2

A second polyurethane containing steroid was produced according to the following two step process.

Step 1

6.68 grams (0.025 Eq.) of dimerol and 13.48 grams (0.226 Eq.) of 1,6-hexane diol were dried under vacuum at 100° C. and then mixed with 49.82 grams (0.167 Eq.) of dimer diisocyanate which had previously been heated to 100° C. The mixture was stirred until a clear solution was formed, and cured overnight under nitrogen for 12 to 16 hours at 50° C. The resulting prepolymer was stored under nitrogen purge at room temperature.

Step 2

7.62 grams (0.009 Eq.) of the hydroxyl terminated prepolymer prepared according to Step 1 were mixed with 8.89 grams (0.033 Eq.) of dimerol which had previously been heated to 110° C. and mixed well. 8.5 grams of dried sodium dexamethasone phosphate were slowly added to and mixed into the mixture. Following this, 3.53 grams (0.042 Eq.) of 1,4-cyclohexane diisocyanate were added to the mixture, and the mixture was heated and stirred at 50° C.–80° C. until the cyclohexane diisocyanate was melted and dispersed. The resulting polymer was placed into picture frame molds and cured overnight at 50° C. under nitrogen purge to form a film of approximately 0.040 inches in thickness.

EXAMPLE 3

A polyurethane approximating the characteristics of Pellethane 5363-80A, incorporating the steroid was prepared according to a two step procedure.

Step 1

43.35 grams (0.300 Eq.) of Isonate 143L, a diisocyanate product of Upjohn was combined with 49.82 grams (0.100 Eq.) of Polymeg 1000, a diol produced by Quaker Oats. The mixture was heated to 50° C. and stirred occasionally until the reaction started to exotherm. The mixture was then held at 50° C. for 16 to 24 hours.

Step 2

9.12 grams (0.02 Eq.) of the isocyanate terminated prepolymer prepared in Step 1 above were added to 0.88 grams (0.02 Eq.) of 1,4-butane diol and 3.46 grams of sodium dexamethasone phosphate. The materials were mixed until homogenous, placed in a picture frame mold and allowed to cure for 16 hours at 50° C. under nitrogen purge.

EXAMPLE 4

A cross-linked version of the polyurethane of Example 1 containing sodium dexamethasone phosphate was produced according to the following polymerization method.

Step 1

10.6 grams (0.013 Eq.) of a hydroxyl terminated prepolymer according to Step 1, Example 1, were prepared and mixed with 5.52 grams (0.047 Eq.) of C20 triol (bis-hydroxymethyl octadecanol), supplied by Henkel, 5.9 grams of sodium dexamethasone phosphate and 4.95 grams (0.060 Eq.) of 1,4-cyclohexane diisocyanate. The resulting mixture was placed in a 200° F. oven under nitrogen purge and slowly mixed periodically until a homogenous mixture was produced. The resultant mixture was poured into a picture frame mold, pressed to form a film of approximately 0.040 inches and cured for 16 to 24 hours at 50° C. Testing of the resultant film by immersion in deionized water indicated some elution of the steroid, but less elution than from the steroid of Example 1, suggesting that elution rate may be affected by the degree of cross-linking of the matrix.

In order to predict whether the steroid incorporated into the above polymers would elute out of the polymers in the presence of body fluid, annular plugs having the configuration illustrated for MCRD 30, FIG. 1, were cut out of the films. All of the MCRD's prepared according to the above examples were generally dimensionally stable in and eluted steroid into deionized water.

Although the above examples set forth specific polymers which are appropriate for fabrication of monolithic controlled release devices, it is believed that other urethanes, and other polymers will also be appropriate. Polyureas and other dimensionally stable, water permeable polymers may also be useful, provided that the conditions required to process the polymers avoid the necessity of application of high levels of heat, which may decrease the potency of the drug incorporated.

If polyureas are used, the first step of the process may comprise the reaction of a diamine or polyamine alone or in conjunction with a diol or polyol with a diisocyanate or polyisocyanate to produce a polyurea or polyurea-polyurethane prepolymer. If the prepolymer is isocyanate terminated, the second step may then comprise mixing the steroid with the prepolymer followed by reaction of the prepolymer with a diamine or polyamine to form a polyurea or with a diol or polyol to form a polyurea-polyurethane. If the prepolymer is amine terminated, the second step may then comprise mixing the steroid with the prepolymer followed by reaction of the prepolymer with a diisocyanate or polyisocyanate alone or in conjunction with a diol or polyol to form a polyurea or polyurethane-polyurea.

It is believed important in the context of the invention, therefore, that the drug be incorporated into the polymer during the polymerization process, and that polymers which may be fabricated using processes which do not exceed 100° C. to 150° C. for any significant length of time.

In conjunction with the above specification, we claim:

1. A medical electrical lead, comprising:
   an elongated insulative lead body having a proximal end and a distal end;
   an elongated conductor having a proximal end and a distal end, mounted within said insulative lead body;
   an electrode assembly having proximal and distal ends, mounted at the distal end of said insulative lead body, comprising an electrode head having a lumen open to the distal end of said electrode assembly;

a fixation helix rotatably mounted within said electrode assembly and having a proximal end located within said lumen of said electrode head and a distal end extending from the distal end of said electrode assembly;

a controlled release device containing a desired drug mounted to said electrode assembly, mounted around said fixation helix, said fixation helix rotatably mounted with respect said controlled release device, said controlled release device having an interior surface surrounding said fixation helix adapted for elution of said desired drug from said interior surface into said lumen of said electrode head, said controlled release device being sufficiently dimensionally stable such that expansion of said controlled release device in the presence of body fluids does not interfere with rotation of said fixation helix; and an electrode surface, mounted to said electrode head, coupled to the distal end of said elongated conductor.

2. A lead according to claim 1 wherein said electrode surface is located on said fixation helix.

3. A medical electrical lead comprising:

an elongated insulative lead body having a proximal end and a distal end;

an elongated conductor having a proximal end and a distal end, mounted within said insulative lead body;

an electrode assembly having proximal and distal ends, mounted at the distal end of said insulative lead body, comprising an electrode head having a lumen open to the distal end of said electrode assembly;

a fixation helix having a proximal end located within said lumen of said electrode head and a distal end extending from the distal end of said electrode assembly;

a controlled release device containing a desired drug and taking the form of a hollow cylinder, mounted within said electrode head, mounted around said fixation helix, said controlled release device having an interior surface surrounding said fixation helix and adapted for elution of said desired drug from said interior surface into said lumen of said electrode head, wherein said electrode head comprises a member having proximal and distal ends and an internal lumen and a cylindrical sleeve having proximal and distal ends mounted external to said member and extending distally from said member, said sleeve having inwardly directed projections around the circumference of said sleeve at the proximal and distal ends of said sleeve, the projections at the proximal end of said sleeve engaging said member, said controlled release device mounted at the distal end of said member, encircled by said sleeve, said inwardly directed projections at the distal end of said sleeve mounted distal to said controlled release device, whereby said controlled release device is mounted to and contained within said electrode head.

4. A lead according to claim 1 or claim 3 further comprising means for advancing said fixation helix from a first position in which the distal end of said helix is adjacent to the distal end of said electrode assembly to a second position in which the distal end of said helix is located distal to the distal end of said electrode assembly.

5. A lead according to claim 4 wherein said helix is advanceable from said first position to said second position by rotation of said helix and wherein said elongated conductor is rotatably mounted within said insulative lead body and mechanically coupled to said fixation helix whereby rotation of said conductor accomplishes rotation and advancement of said fixation helix from said first position to said second position.

6. A lead according to claim 1 or claim 3 wherein said controlled release device comprises a dimensionally stable release device compounded of said desired drug located within a desired polymer.

7. A lead according to claim 6 wherein said polymer comprises a polyurethane, polyurea or polyurethane-polyurea.

8. A lead according to claim 1 or claim 3 wherein said controlled release device is adhesively mounted to said electrode assembly.

9. A lead according to claim 3 wherein said member and said controlled release device are both fabricated of polyurethanes and wherein said controlled release device is adhesively bonded to said member.

* * * * *